(12) United States Patent
Gemma et al.

(10) Patent No.: US 12,357,255 B2
(45) Date of Patent: Jul. 15, 2025

(54) MAMMOGRAPHY APPARATUS

(71) Applicant: FUJIFILM Corporation, Tokyo (JP)

(72) Inventors: Kohei Gemma, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 212 days.

(21) Appl. No.: 18/454,618

(22) Filed: Aug. 23, 2023

(65) Prior Publication Data

US 2024/0065659 A1 Feb. 29, 2024

(30) Foreign Application Priority Data

Aug. 30, 2022 (JP) .................. 2022-137268

(51) Int. Cl.
*A61B 6/00* (2024.01)
*A61B 6/04* (2006.01)
*A61B 6/46* (2024.01)
*A61B 6/50* (2024.01)

(52) U.S. Cl.
CPC ............ *A61B 6/502* (2013.01); *A61B 6/0414* (2013.01); *A61B 6/462* (2013.01)

(58) Field of Classification Search
CPC ......... A61B 6/502; A61B 6/0414; A61B 6/50; A61B 6/0421; A61B 6/461; A61B 6/462; A61B 6/463; A61B 6/464; A61B 6/465; A61B 6/00; A61B 6/08; A61B 6/04
See application file for complete search history.

(56) References Cited

U.S. PATENT DOCUMENTS

| | | |
|---|---|---|
| 2008/0087830 A1 | 4/2008 | Kashiwagi |
| 2022/0096025 A1 | 3/2022 | Fujimoto et al. |
| 2022/0096031 A1 | 3/2022 | Konno et al. |
| 2022/0101553 A1* | 3/2022 | Konno .................. G06T 7/0012 |

FOREIGN PATENT DOCUMENTS

| | | |
|---|---|---|
| JP | 2007-236805 A | 9/2007 |
| WO | 2020/069031 A1 | 4/2020 |

OTHER PUBLICATIONS

The extended European search report issued by the European Patent Office on Jan. 4, 2024, which corresponds to European Patent Application No. 23194064.4-1126 and is related to U.S. Appl. No. 18/454,618.

* cited by examiner

*Primary Examiner* — Don K Wong

(74) *Attorney, Agent, or Firm* — Studebaker Brackett PLLC

(57) ABSTRACT

A mammography apparatus includes: an imaging table; a radiation source; a compression plate that compresses the breast and is movable between the radiation source and the imaging table; a projector that includes a display displaying an image including first information projected onto a first surface facing the radiation source on the imaging table and second information projected onto a second surface facing the radiation source on the compression plate, and a projection optical system, in which a focus of the projection optical system is adjusted in accordance with a projection distance to the first surface; and a processor that is configured to control the display and change at least one of a display size or a display position of the second information in the image on an image display surface of the display in accordance with movement of the compression plate having the second surface independently of the first information.

7 Claims, 11 Drawing Sheets

FIG. 9

| INFORMATION TO BE PROJECTED | PROJECTION CONDITION | | | |
|---|---|---|---|---|
| | PROJECTION LOCATION | DISPLAY POSITION, DISPLAY SIZE | FOCUS OF PROJECTION OPTICAL SYSTEM | PROJECTION MAGNIFICATION OF PROJECTION OPTICAL SYSTEM |
| SKIN LINE (FIRST INFORMATION) | PROJECTION LOCATION | FIXED | FIXED ON IMAGING SURFACE | FIXED |
| IMAGING CONDITION INFORMATION (SECOND INFORMATION) | BOTTOM SURFACE OF COMPRESSION PLATE | ADJUST IN ACCORDANCE WITH HEIGHT OF COMPRESSION PLATE | FIXED ON IMAGING SURFACE | FIXED |

MAMMOGRAPHY APPARATUS

CROSS-REFERENCE TO RELATED APPLICATION

This application claims priority from Japanese Patent Application No. 2022-137268, filed Aug. 30, 2022, the disclosure of which is incorporated herein by reference in its entirety.

BACKGROUND

Technical Field

The present disclosure relates to a mammography apparatus.

Related Art

JP2007-236805A discloses an X-ray diagnostic apparatus for mammography comprising: X-ray exposure means for exposing X-rays, an X-ray plane detector for detecting X-rays incident on a detection surface, a compression plate for compressing and fixing a breast, and projection means for projection a reference image which is referred to in a case of fixing the breast by the compression plate onto the compression plate or the detection surface. The technology described in JP2007-236805A discloses that the projection means (for example, a projector) is used to project the reference image (for example, a skin line) for positioning the breast onto the compression plate or the detection surface.

There is a desire to display different information on each of the compression plate and the detection surface. However, the compression plate and the detection surface differ in a projection distance from the projector. Moreover, while a height of the detection surface is fixed so that the projection distance is fixed, a height of the compression plate changes so that the projection distance also changes. In this case, as a solution for appropriately adjusting a projection magnification and a focus of the information to be projected onto each of the compression plate and the detection surface, it is conceivable to provide a focus adjustment mechanism depending on a place where an image is projected, or to use a different projector for each place where the image is projected.

However, in a case where the focus adjustment mechanism is provided depending on the place where the image is projected or the different projector is used for each place where the image is projected, a configuration becomes complicated. The technology of the present disclosure provides a mammography apparatus capable of performing appropriate projection onto two surfaces having different projection distances while suppressing complication of the configuration as compared with a case where the present configuration is not used.

SUMMARY

A first aspect according to the technology of the present disclosure is a mammography apparatus comprising: an imaging table on which a breast is placed; a radiation source that emits radiation toward the breast; a compression plate that compresses the breast on the imaging table and is movable between the radiation source and the imaging table; a projector that includes a display displaying an image including first information projected onto a first surface facing the radiation source on the imaging table and second information projected onto a second surface facing the radiation source on the compression plate, and a projection optical system projecting the image toward the first surface and the second surface, in which a focus of the projection optical system is adjusted in accordance with a projection distance to the first surface; and a processor that is configured to control the display and change at least one of a display size or a display position of the second information in the image on an image display surface of the display in accordance with movement of the compression plate having the second surface independently of the first information.

A second aspect according to the technology of the present disclosure is the mammography apparatus according to the first aspect, in which a display size and a display position of the first information in the image are set in advance in accordance with the projection distance to the first surface and are fixed even in a case where the display size or the display position of the second information changes.

A third aspect of the technology of the present disclosure is the mammography apparatus according to the first aspect, in which the focus of the projection optical system is adjusted within a range between the first surface and a position close to a projector side from the first surface by a statistically determined thickness of the breast.

A fourth aspect according to the technology of the present disclosure is the mammography apparatus according to the third aspect, in which the focus of the projection optical system is adjusted to the first surface.

A fifth aspect of the technology of the present disclosure is the mammography apparatus according to the first aspect, in which, on the second surface of the compression plate, a region onto which the second information is projected is subjected to light transmission suppression processing for suppressing transmission of light.

A sixth aspect according to the technology of the present disclosure is the mammography apparatus according to the first aspect, in which the first information is a skin line indicating a contour of the breast, which is an index for placing the breast.

A seventh aspect according to the technology of the present disclosure is the mammography apparatus according to the first aspect, in which the second information is an imaging condition for imaging the breast.

The technology of the present disclosure can provide a mammography apparatus capable of performing appropriate projection onto two surfaces having different projection distances while suppressing complication of a configuration.

BRIEF DESCRIPTION OF THE DRAWINGS

FIG. 9 is a diagram for explaining a projection position, a display position, a size, and a focus in the mammography apparatus.

DETAILED DESCRIPTION

Hereinafter, an embodiment of the present disclosure will be described in detail with reference to the drawings.

Figure 1:
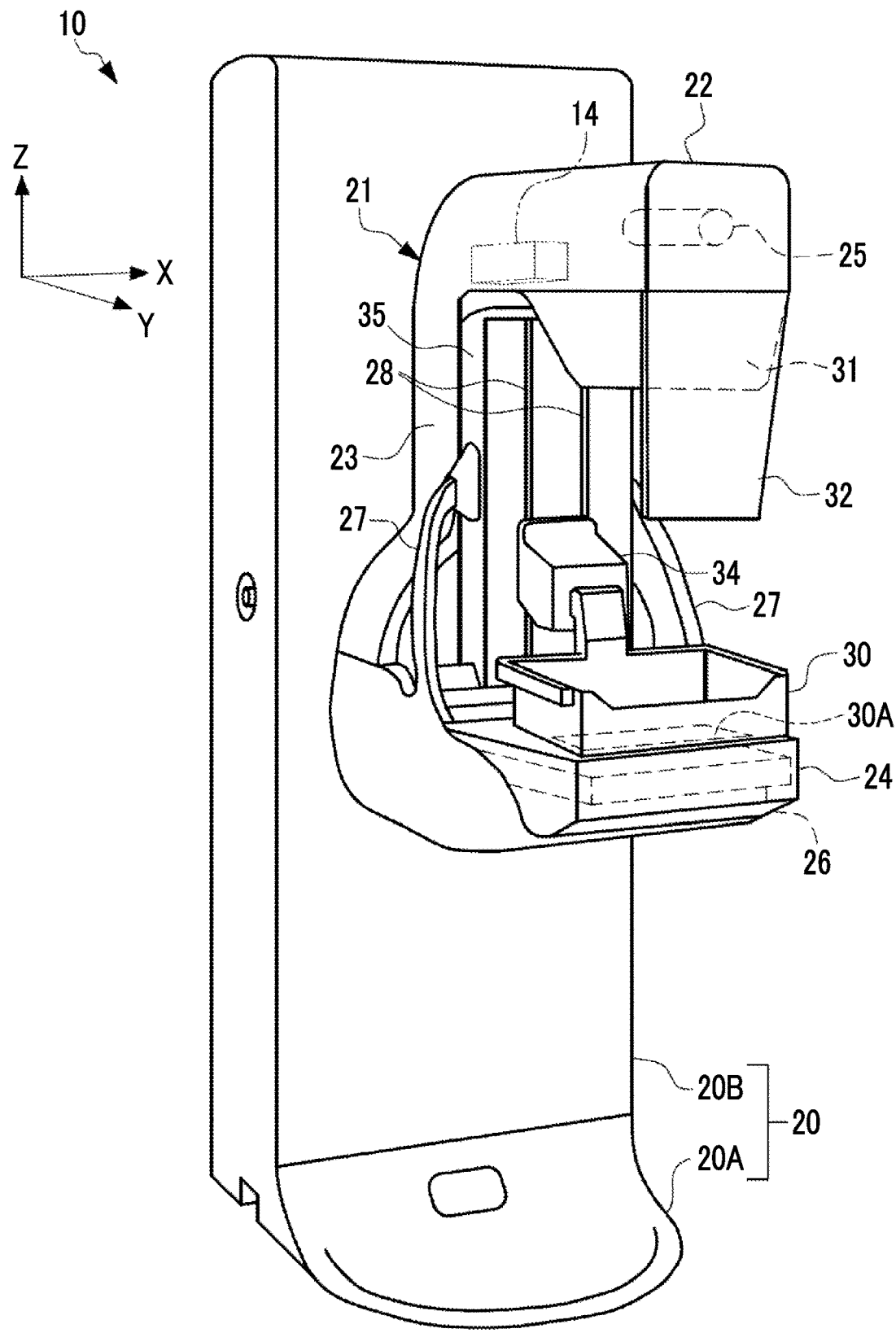
FIG. 1 is an external perspective view showing an example of a configuration of a mammography apparatus.
Figure 2:
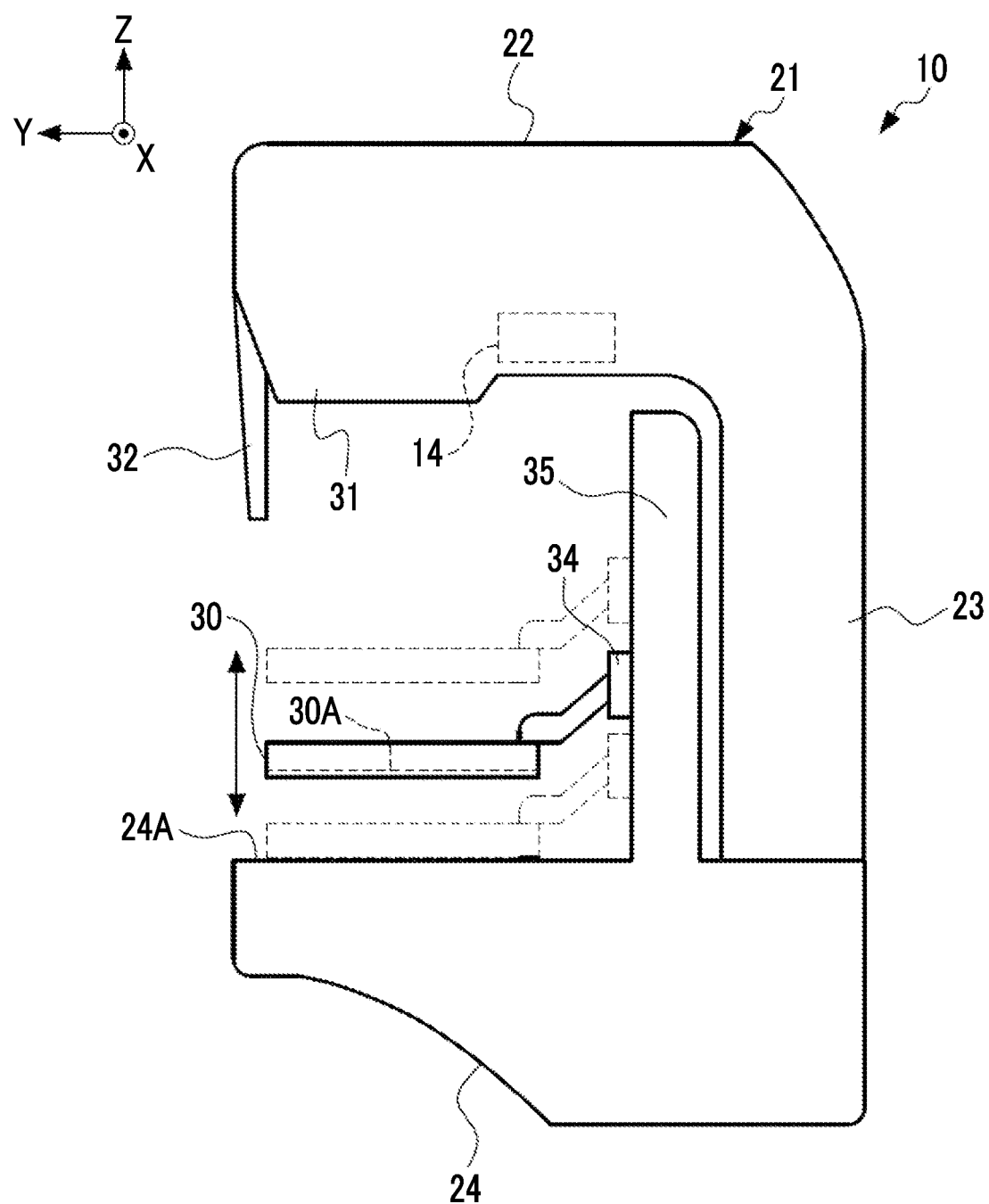
FIG. 2 is an external side view showing an example of the configuration of the mammography apparatus.

As shown in FIGS. 1 and 2, a mammography apparatus 10 according to a first embodiment is a radiography apparatus that irradiates a breast M (see FIG. 4) of a subject to be examined with radiation and captures a radiographic image of the breast M. The radiation is X-rays as an example, but γ-rays may also be used.

The mammography apparatus 10 is connected to a console (not shown). The console has a setting function of setting the mammography apparatus 10 in accordance with an imaging order and a function of acquiring a radiographic image captured by the mammography apparatus 10 and displaying the acquired radiographic image. The console is communicably connected to an image database server (not shown) via a network (not shown) such as a local area network (LAN).

The mammography apparatus 10 includes a stand 20 and an arm 21. The stand 20 includes a pedestal 20A that is provided on a floor of a radiography room and a support column 20B that extends from the pedestal 20A in a height direction. The arm 21 has a substantially C-shape as viewed sidewise and is connected to the support column 20B. Since the arm 21 is movable in a height direction with respect to the support column 20B, a height of the arm 21 can be adjusted according to a height of the subject. The arm 21 is rotatable about a rotation axis perpendicular to the support column 20B.

The arm 21 is composed of a radiation source accommodation portion 22, a main body portion 23, and an imaging table 24. A radiation source 25 is accommodated in the radiation source accommodation portion 22. The breast M of the subject is placed on the imaging table 24. The imaging table 24 is an example of an "imaging table" according to the technology of the present disclosure. A radiation detector 26 is accommodated in the imaging table 24. The main body portion 23 integrally connects the radiation source accommodation portion 22 and the imaging table 24. The main body portion 23 holds the radiation source accommodation portion 22 and the imaging table 24 at positions facing each other. Handrails 27 for the subject to hold are provided on both sides of the main body portion 23.

The radiation source 25 emits radiation toward the breast M placed on the imaging table 24. The radiation source 25 is an example of a "radiation source" according to the technology of the present disclosure. The radiation emitted from the radiation source 25 is transmitted through the compression plate 30 and then is incident on the breast M. The radiation detector 26 detects the radiation transmitted through the breast M and outputs a radiographic image. The radiation detector 26 is referred to as a flat panel detector (FPD). The radiation detector 26 may be an indirect conversion type that includes a scintillator converting the radiation into visible light and converts the visible light emitted from the scintillator into an electric signal or a direct conversion type that directly converts the radiation into an electric signal.

An irradiation field limiter 31 is provided between the radiation source accommodation portion 22 and the imaging table 24. The irradiation field limiter 31 is also referred to as a collimator and defines an irradiation field of the radiation to the imaging table 24.

A face guard 32 is attached to the radiation source accommodation portion 22. The face guard 32 is formed of or coated with a material not transmitting the radiation and protects a face of the subject from the radiation.

The compression plate 30 is provided between the imaging table 24 and the irradiation field limiter 31 to sandwich the breast M with the imaging table 24 and compress the breast M. The compression plate 30 is an example of a "compression plate" according to the technology of the present disclosure. The compression plate 30 is formed of a material that transmits the radiation. The compression plate 30 is disposed at a position facing the imaging table 24. In the present embodiment, the compression plate 30 has a box shape in which an upper surface side is open. The compression plate 30 may have other shapes such as a flat plate shape.

A projector 14 is accommodated in the radiation source accommodation portion 22. The projector 14 projects an image toward an imaging surface 24A of the imaging table 24. Here, the imaging surface 24A is a surface facing the radiation source 25 on the imaging table 24. In addition, the projector 14 projects an image toward a surface facing the radiation source 25 on the compression plate 30. Since the compression plate 30 of the present embodiment has a box shape, a bottom surface 30A of the box shape is a surface facing the radiation source 25. The projector 14 projects an image toward the bottom surface 30A of the compression plate 30. The projector 14 is an example of a "projector" according to the technology of the present disclosure. The imaging surface 24A is an example of a "first surface" according to the technology of the present disclosure, and the bottom surface 30A is an example of a "second surface" according to the technology of the present disclosure.

A drive mechanism 35 movably supports the compression plate 30 between the radiation source 25 and the imaging table 24. Further, a movable portion 34 is disposed between the compression plate 30 and the drive mechanism 35. The movable portion 34 is slidably held by a rail 28 provided in the drive mechanism 35. The rail 28 extends in an up-down direction.

The compression plate 30 is attached to the movable portion 34. The movable portion 34 moves in the up-down direction together with the compression plate 30 by the drive mechanism 35 described later. The up-down direction is functionally a direction in which the compression plate 30 moves toward the imaging table 24 (downward direction) and a direction in which the compression plate 30 moves away from the imaging table 24 (upward direction). As described above, the compression plate 30 is configured to be movable in such a manner that a distance from the imaging table 24 is changed.

Figure 3:
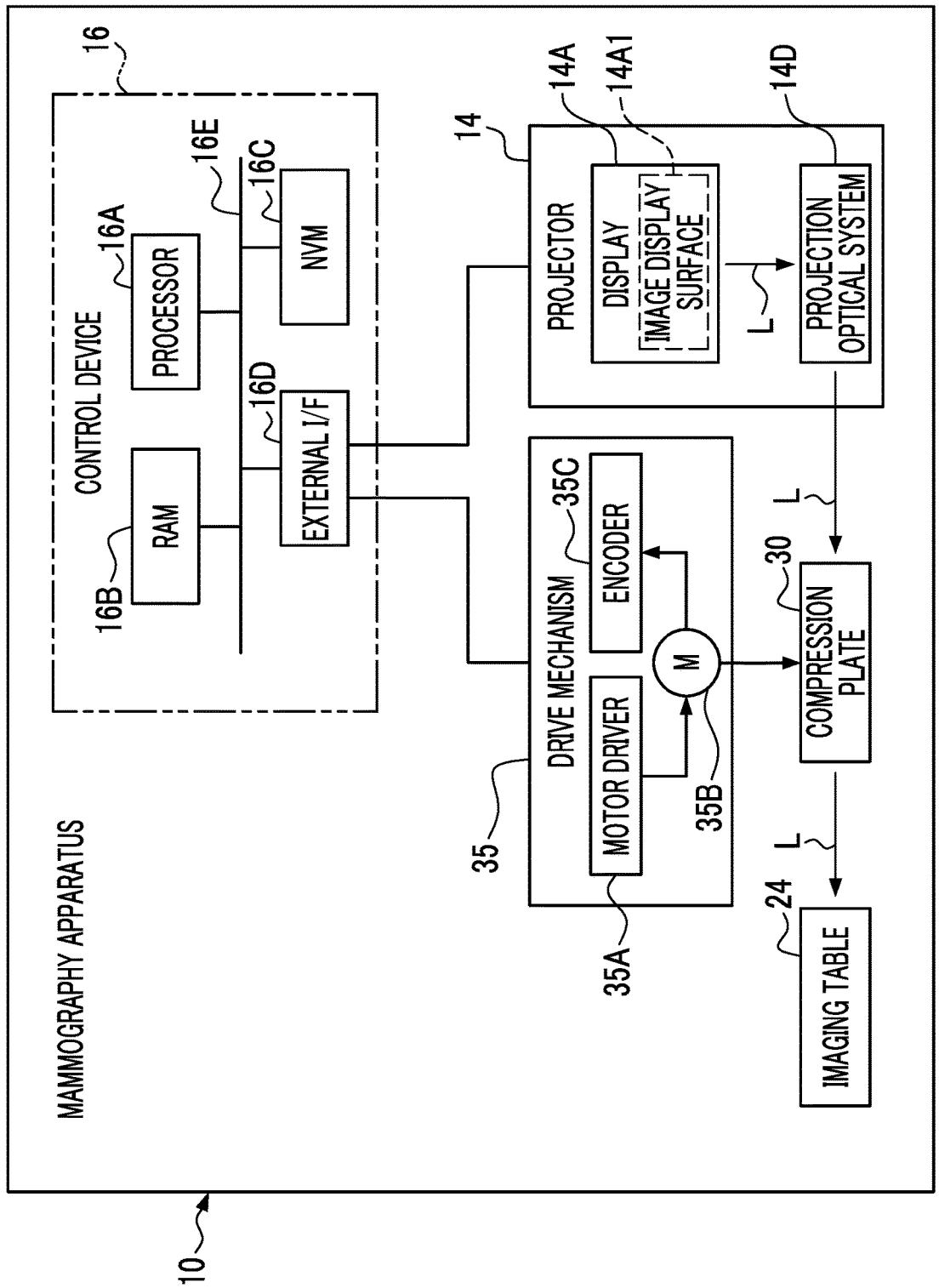
FIG. 3 is a block diagram showing an example of the configuration of the mammography apparatus.

As shown in FIG. 3, the mammography apparatus 10 comprises a control device 16. The control device 16 comprehensively controls the operation of each part of the mammography apparatus 10, such as the radiation source 25, the radiation detector 26, the arm 21, the drive mechanism 35, and the projector 14. In FIG. 3, control targets of the control device 16 are shown only for the drive mechanism 35 and the projector 14, and the others are not shown.

The control device 16 comprises, for example, a processor 16A, a random access memory (RAM) 16B, a non-volatile memory (NVM) 16C, and an external interface (I/F) 16D.

The processor 16A, the RAM 16B, the NVM 16C, and the external I/F 16D are electrically connected via a bus 16E. The processor 16A is an example of a "processor" according to the technology of the present disclosure.

The processor 16A is, for example, a central processing unit (CPU), controls each part, and performs image processing as described later. The RAM 16B is a memory in which information is temporarily stored, and is used as a work memory by the processor 16A. The NVM 16C is a non-volatile storage device that stores various programs, various parameters, and the like. Examples of the NVM 16C include a flash memory (for example, an electrically erasable and programmable read only memory (EEPROM) and/or a solid state drive (SSD). The flash memory is merely an example, and other non-volatile storage devices, such as a hard disk drive (HDD), may be employed or a combination of two kinds or more of non-volatile storage devices may be employed.

The external OF 16D manages the exchange of information between the control device 16, and the projector 14 and the drive mechanism 35. The external OF 16D outputs, for example, a signal for emitting projection light L representing an image to be projected to the projector 14. In addition, the external OF 16D outputs, for example, a signal for controlling the operation of the drive mechanism 35 to the drive mechanism 35.

Figure 4:
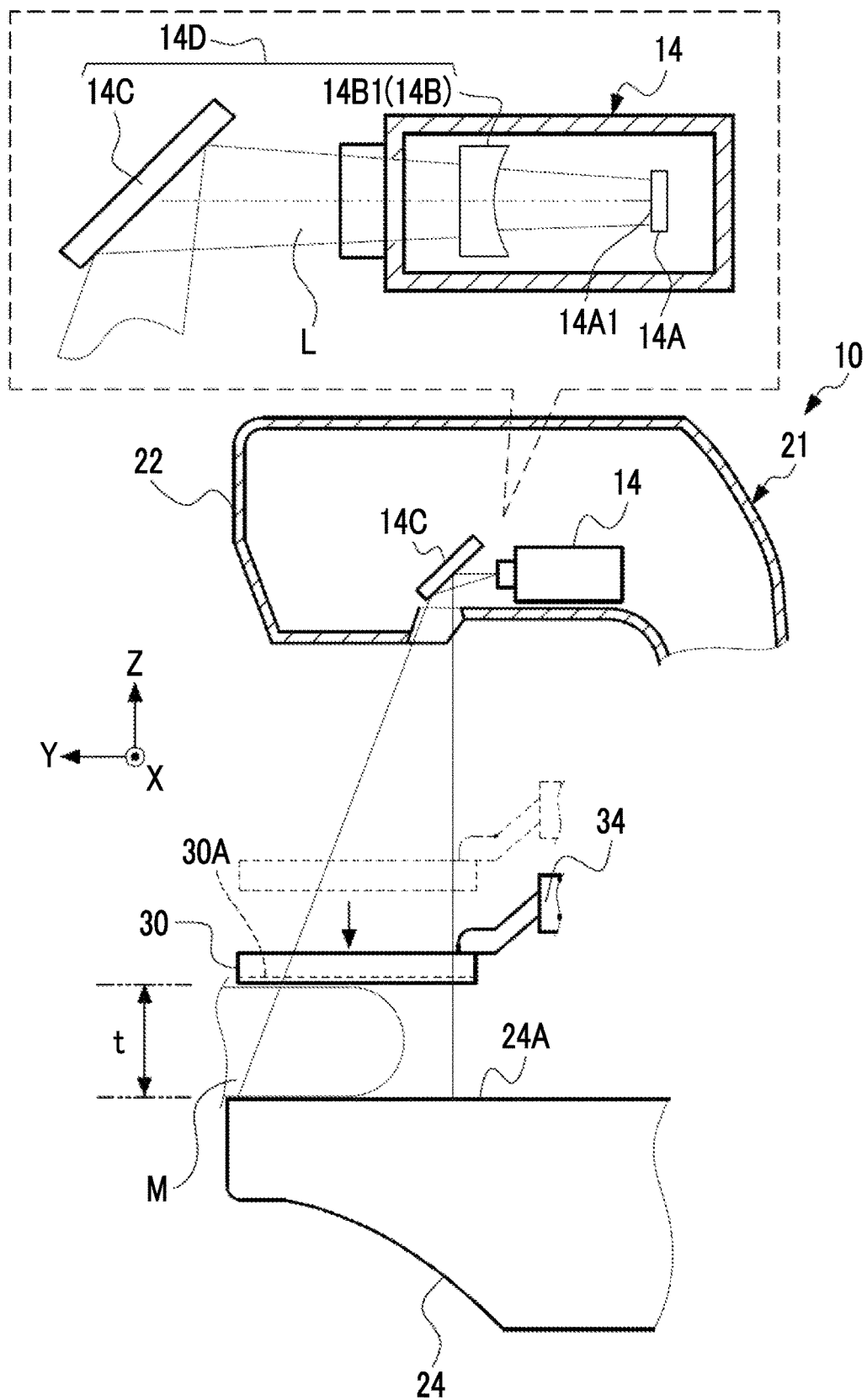
FIG. 4 is a side view showing an example of projection of an image in the mammography apparatus.

The projector 14 comprises a display 14A that displays an image to be projected and a projection optical system 14D that magnifies and projects the image displayed on the display 14A (see also FIG. 4). The control device 16 controls the display of the image on an image display surface 14A1 of the display 14A. The display 14A is an example of a "display" according to the technology of the present disclosure, and the image display surface 14A1 is an example of an "image display surface" according to the technology of the present disclosure. Examples of the display 14A include a digital micromirror device (DMD) or a liquid crystal display (LCD). As is well known, the DMD comprises a plurality of micromirrors corresponding to a plurality of pixels. As an example, by changing an angle of each micromirror, a reflection direction of light from a light source is changed between on-light that is incident on the projection optical system 14D and off-light that is not incident on the projection optical system 14D. Then, a light quantity for each pixel is adjusted according to the duration of the on-light. In this way, optical modulation is performed to put information about the image to be projected on the projection light L by changing the angles of the plurality of micromirrors corresponding to the plurality of pixels. In a case where the display 14A is the DMD, an arrangement surface on which the plurality of micromirrors are two-dimensionally arranged corresponds to the image display surface 14A1, and the control of the micromirrors according to the image to be projected corresponds to the image display. As is well known, the LCD comprises a plurality of liquid crystal cells corresponding to a plurality of pixels, and changes a transmission state of the light from the light source for each liquid crystal cell to perform the optical modulation according to the image to be projected. In a case where the display 14A is the LCD, an arrangement surface on which the plurality of liquid crystal cells are two-dimensionally arranged corresponds to the image display surface 14A1. Although the display 14A is schematically shown in FIGS. 3 and 4, the display 14A includes a light source. In addition, as the display 14A, self-luminous light emitting elements such as organic EL elements may be arranged two-dimensionally to function as the image display surface 14A1.

The projection light L emitted from the display 14A is incident on the projection optical system 14D, passes through the projection optical system 14D, and is projected onto the bottom surface 30A of the compression plate 30. Further, the projection light L that has passed through the compression plate 30 is projected onto the imaging surface 24A of the imaging table 24. The projection optical system 14D includes a plurality of optical elements, magnifies an image generated in the display 14A, and projects the image toward the compression plate 30 and the imaging table 24. The projection optical system 14D is composed of a built-in optical system 14B incorporated inside a main body of the projector 14 and an optical element disposed outside the main body of the projector 14. For example, the built-in optical system 14B includes one or more lenses 14B1 as optical elements. The optical element disposed outside the main body is a mirror 14C in this example. For example, the mirror 14C is disposed in a posture inclined by 45° with respect to an optical axis of the built-in optical system 14B, and changes a propagation path of the projection light L emitted from the built-in optical system 14B by 90° toward the compression plate 30 and the imaging table 24. A focus of the projection optical system 14D is adjusted in advance in accordance with a projection distance of the imaging table 24 to the imaging surface 24A. The built-in optical system 14B is an example of a "projection optical system" according to the technology of the present disclosure. In addition, although an aspect in which the focus of the projection optical system 14D is adjusted in advance before the projection of the image is performed has been described here, the technology of the present disclosure is not limited to this. As long as the image is projected in a state in which the focus is adjusted according to the projection distance of the imaging table 24 to the imaging surface 24A, for example, an aspect in which the focus adjustment is performed within a predetermined time (for example, 2 to 3 seconds) from the start of projection may be employed.

The drive mechanism 35 includes a motor driver 35A, a motor 35B, and an encoder 35C. The motor driver 35A operates the motor 35B based on a signal output from the processor 16A via the external OF 16D. The motor 35B rotates in response to an electric drive signal output by the motor driver 35A and moves the compression plate 30 via a power transmission mechanism (for example, a feed screw mechanism) (not shown). The encoder 35C converts an amount of mechanical displacement of the rotation of the motor 35B into an electric signal and outputs the electric signal to the processor 16A.

The encoder 35C is used to detect a movement amount of the compression plate 30. The encoder 35C is, for example, a rotary encoder in which a photosensor is combined with a rotary plate in which a plurality of small holes that transmit light are arranged on a circumference at regular intervals and that rotates together with a rotary shaft of the motor 35B. As is well known, the rotary encoder receives pulsed beams intermittently output from the small holes with the rotation of the rotary plate by the photosensor, and outputs an encoder pulse according to the number of the received pulsed beams. The encoder pulse is an example of an electric signal representing the amount of mechanical displacement of the rotation of the motor 35B. The processor 16A derives a rotation amount of the motor 35B by counting the encoder pulse and detects the movement amount of the compression plate 30 from the derived rotation amount. The encoder 35C may be a linear encoder that detects the movement amount of the compression plate 30 instead of the rotary encoder. Further, a pulse motor may be used as the motor 35B, and the movement amount of the compression plate 30 may be detected by counting drive pulses output by the processor 16A to the motor 35B.

Figure 5:
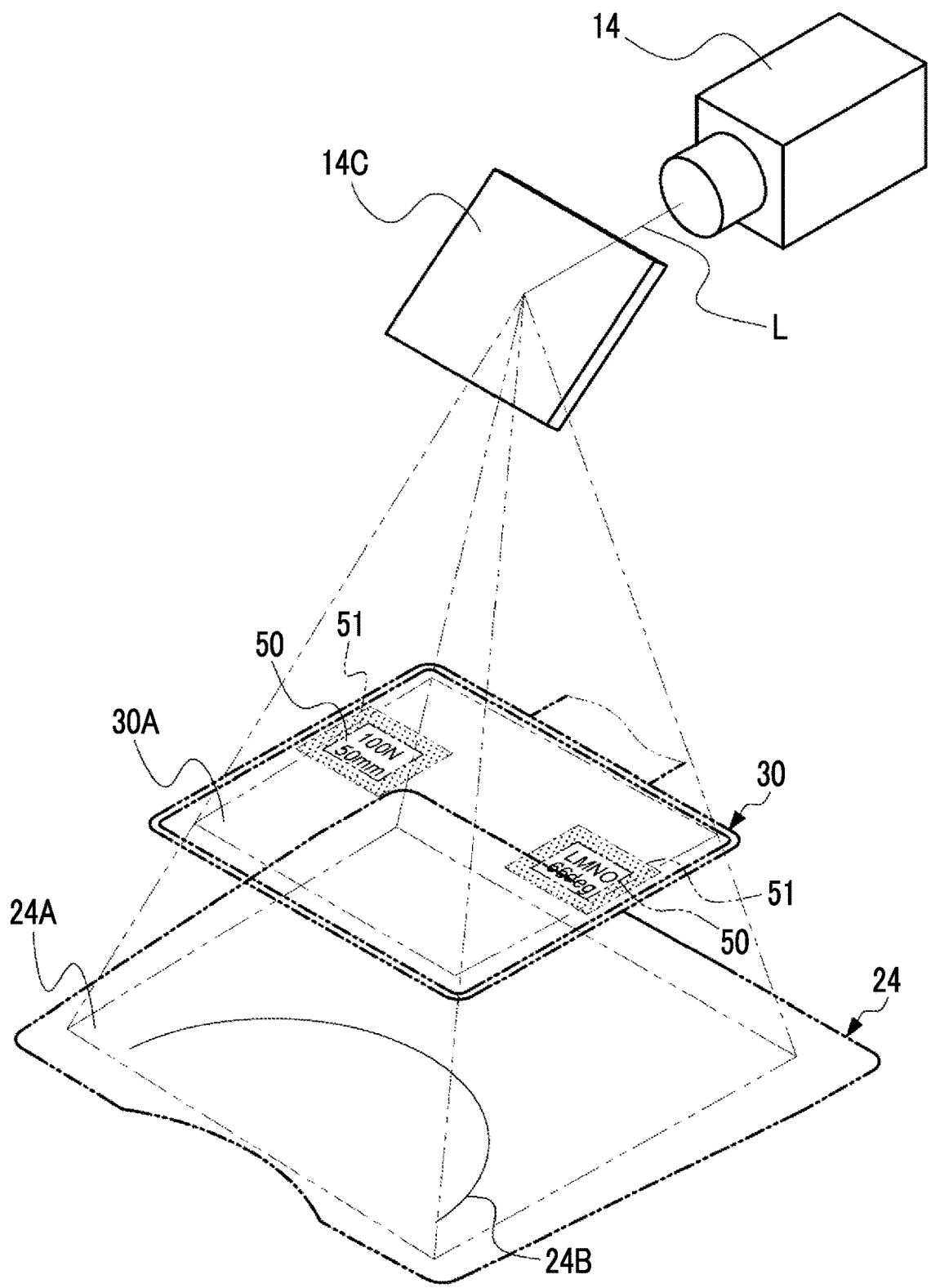
FIG. 5 is a schematic diagram showing an example of the projection of the image in the mammography apparatus.

As shown in FIGS. 4 and 5, in the mammography apparatus 10, information is projected onto the imaging surface 24A and the bottom surface 30A of the compression plate 30 by emitting the projection light L from the projector 14. The projector 14 can project different information onto each of the imaging surface 24A and the bottom surface 30A of the compression plate 30.

Imaging condition information 50, which is information indicating imaging conditions, is projected onto the bottom surface 30A of the compression plate 30. Examples of the imaging condition include a current compression pressure, compression thickness t, or type of imaging technique for the breast M. The compression pressure is obtained, for example, by measuring a reaction force applied to the compression plate 30 in a case where the breast M is compressed by the compression plate 30 with a pressure measuring device (not shown). The pressure measuring device is provided, for example, on the imaging table 24. The compression thickness t is obtained by measuring a height of the compression plate 30 with respect to the imaging surface 24A in a state in which the breast M is compressed. The height of the compression plate 30 is measured, for example, based on the movement amount of the compression plate 30 which is detected by the encoder 35C. Examples of the imaging technique include craniocaudal (CC) imaging in which the breast M is compressed from a cranio-caudal direction of the subject and imaged, medio-lateral (MLO) imaging in which the breast M is compressed from a direction inclined with respect to the cranio-caudal direction of the subject and imaged, and the like. For example, the imaging technique is input in advance by an operator. In addition, examples of other imaging conditions include past imaging conditions (compression pressure, compression thickness t, type of imaging technique, and the like). Furthermore, other imaging conditions include information that can identify the subject (for example, a name, gender, age, identification (ID) of the subject), or the like. Furthermore, other imaging conditions include information related to mammography examination (an examination date and time, an examination performer, a radiation irradiation time, an output or tube voltage of a radiation source during radiation irradiation, or the like). The imaging condition information 50 is an example of "second information" according to the technology of the present disclosure.

In the bottom surface 30A of the compression plate 30, a region 51 onto which the imaging condition information 50 is projected is subjected to processing for suppressing transmission of light. In an example shown in FIG. 6, the region 51 onto which the imaging condition information 50 is projected is subjected to a roughening treatment. As a result, the projection light L representing the imaging condition information 50 is less likely to transmit through the compression plate 30, and an amount of reflected light on the compression plate 30 increases. Accordingly, the imaging condition information 50 is clearly visible on the compression plate 30. Here, examples of the roughening treatment include blasting. In addition, as another example of the processing for suppressing the transmission of light, a member that is opaque to the projection light L may be attached to the region 51 of the compression plate 30 onto which the imaging condition information 50 is projected. For example, an aspect in which a seal is attached to the region 51 of the compression plate 30 may be employed.

Figure 6:
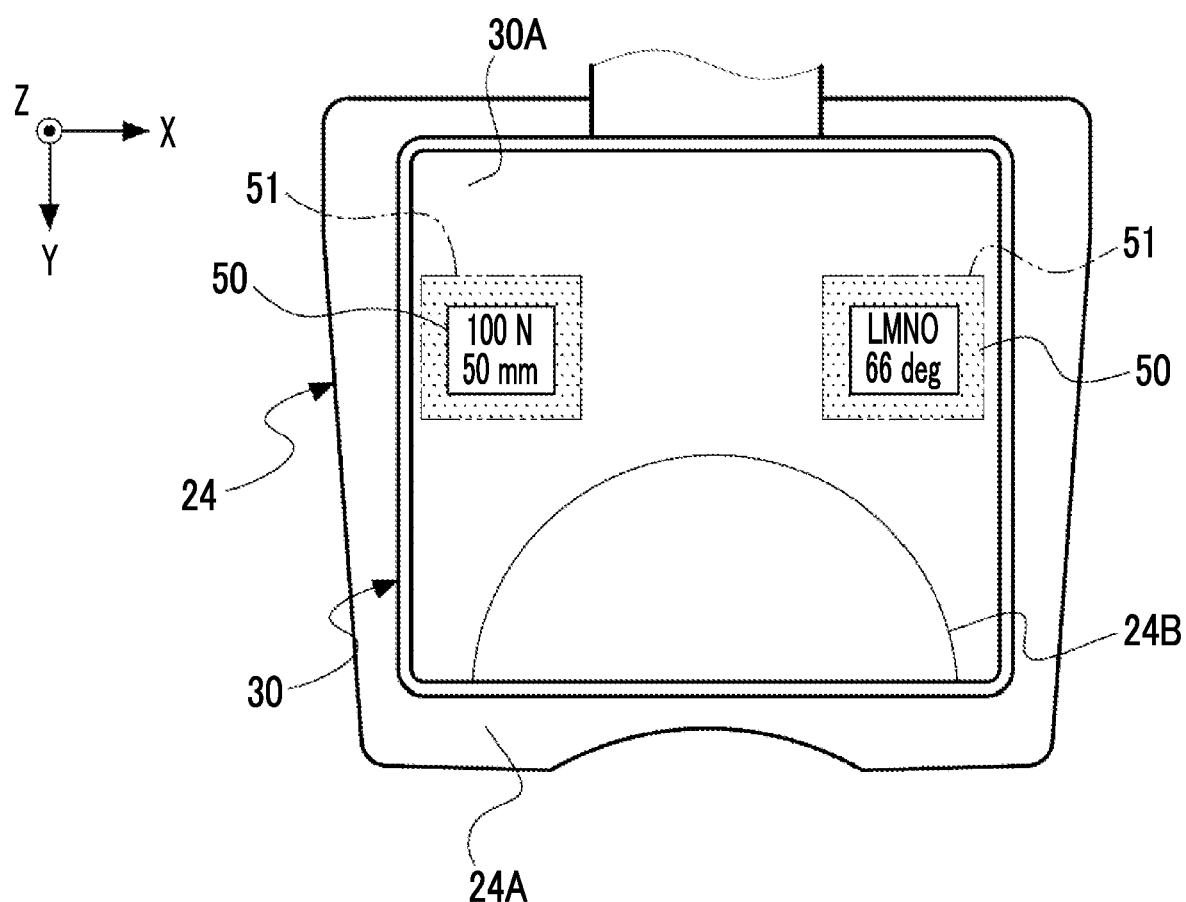
FIG. 6 is a plan view showing an example of a projected image in the mammography apparatus.

Portions of the compression plate 30 other than the region 51 are made of a material transparent to the projection light L. Therefore, the projection light L transmitted through the compression plate 30 is projected onto the imaging surface 24A. A skin line 24B indicating a contour of the breast M, which is an index for placing the breast M, is projected onto the imaging surface 24A. The contour of the breast M indicated by the skin line 24B is obtained by extracting the contour of the breast M from an examination image captured in the past examination. Since a relative positional relationship between the imaging surface 24A and a detection surface of the radiation detector 26 is known, a projection position of the skin line 24B to be projected onto the imaging surface 24A can be derived from a position of the skin line appearing in the examination image detected by the radiation detector 26. By displaying the skin line 24B obtained in the past examination in this way, it is possible to image the breast M at the same position as that of the past examination, which is effective in performing follow-up observation or the like. The skin line 24B is an example of "first information" according to the technology of the present disclosure. The breast M of the subject is positioned on the imaging surface 24A of the imaging table 24 by the user. The breast M is compressed by the compression plate 30 in a state in which the breast M is positioned. Then, as shown in FIGS. 5 and 6, the imaging condition information 50 is projected onto the compression plate 30, and the skin line 24B is projected onto the imaging surface 24A. In addition, instead of the skin line 24B or together with the skin line 24B, a mark indicating a position of a papilla of the breast M (for example, a mark of a cross having an intersection at the position of the papilla) may be projected onto the imaging surface 24A.

For example, a projection magnification of the projection optical system 14D is set such that an image having the maximum size that can be displayed on the image display surface 14A1 falls within a range of the imaging surface 24A. Therefore, among pieces of information displayed on the image display surface 14A1, all of pieces of information carried by the projection light L that reaches the imaging surface 24A are projected onto the imaging surface 24A.

Figure 7:
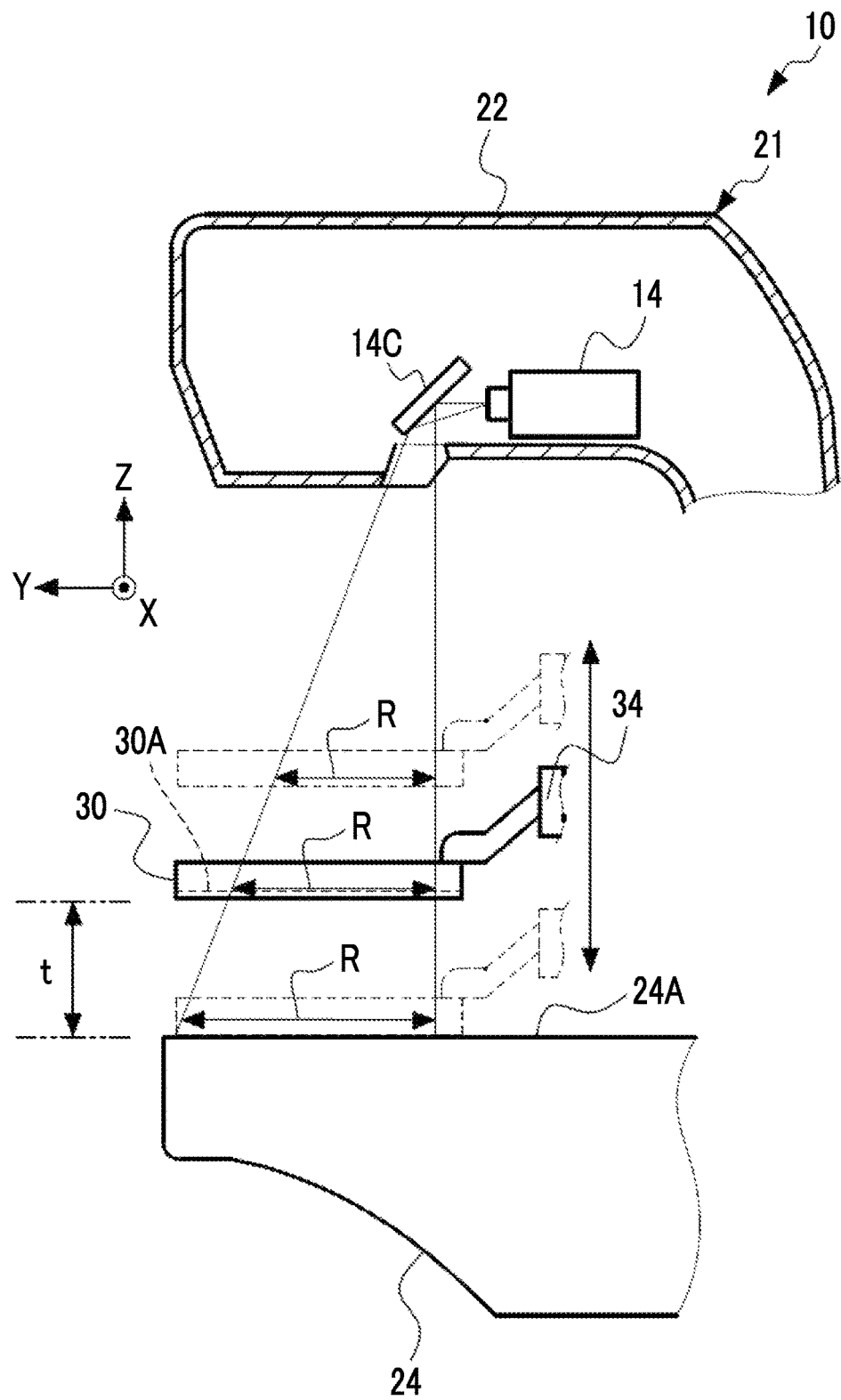
FIG. 7 is a side view showing an example of the projection of the image in the mammography apparatus.

Here, as shown in FIG. 7, the compression plate 30 moves in the up-down direction (a direction along a Z direction shown in FIG. 7). Accordingly, a distance between the compression plate 30 and the projector 14 changes. Therefore, even in a case where the projection magnification of the projection optical system 14D is fixed, a projection distance of an image from the projector 14 to the compression plate 30 changes, so that a projection range R in the compression plate 30 changes. More specifically, a display size of the imaging condition information 50 on the compression plate 30 changes. For example, the display size of the imaging condition information 50 is the smallest on a side where the compression plate 30 is closest to the projector 14, and the display size of the imaging condition information 50 increases as a distance from the projector 14 increases. Then, the display size of the imaging condition information 50 is maximized at a position farthest from the projector 14. In addition, a display position in the compression plate 30 may change due to a change in the display size depending on a direction in which a luminous flux of the projection light L is incident on the compression plate 30. In this way, at least one of the display size or the display position of the imaging condition information 50 changes by the movement of the compression plate 30. Therefore, the imaging condition information 50 may extend beyond the compression plate 30, or the imaging condition information 50 may be too small to decipher the contents. As a result, a visibility of the imaging condition information 50 by the user is reduced.

On the other hand, on the imaging surface 24A, since the projection distance from the projector 14 is constant, a display size of the skin line 24B projected from the projector 14 does not change. Further, as described above, the focus of the projection optical system 14D of the projector 14 is also adjusted in advance in accordance with a distance to the imaging surface 24A. For example, the focus of the projection optical system 14D is optically set based on the arrangement of the optical elements of the projection optical system 14D, the distance between the imaging surface 24A and the projector 14, and the like. For example, the focus of the projection optical system 14D is adjusted within a range between the imaging surface 24A and a position close to the projector 14 from the imaging surface 24A by a statistically determined thickness t of the breast M. Here, the statistically determined thickness t of the breast M is, for example, an average value of thicknesses t of the breasts M of a plurality of subjects, but this is only an example. For example, the statistically determined thickness t of the breast M may be a mode value or a median value of the thicknesses t of the breasts M of a plurality of subjects. In this example, the focus of the projection optical system 14D is on the imaging surface 24A.

As described above, in the mammography apparatus 10, the imaging condition information 50 is projected onto the compression plate 30 where a projection distance from the projector 14 changes, and the skin line 24B is projected onto the imaging surface 24A where the projection distance does not change. In this case, for example, two projectors, that is, a projector for projecting the imaging condition information 50 onto the compression plate 30 and a projector for projecting the skin line 24B onto the imaging surface 24A may be mounted on the mammography apparatus 10, but the configuration of the mammography apparatus 10 becomes complicated.

Therefore, in the mammography apparatus 10 according to the present embodiment, the processor 16A controls the display 14A of one projector 14 to realize appropriate projection on two surfaces having different projection distances such that the skin line 24B is projected onto the imaging surface 24A and the imaging condition information 50 is projected onto the bottom surface 30A of the compression plate 30. First, information displayed on the display 14A of the projector 14 is an image 52 including the imaging condition information 50 and the skin line 24B (see FIGS. 8, 10, and 11). Then, the processor 16A controls the display 14A to change the display size and the display position of the imaging condition information 50 of the image 52 on the image display surface 14A1 in accordance with the movement of the compression plate 30 independently of the display size and the display position of the skin line 24B. In addition, the processor 16A sets in advance the display size and the display position of the skin line 24B of the image 52 on the image display surface 14A1 of the display 14A.

Figure 8:
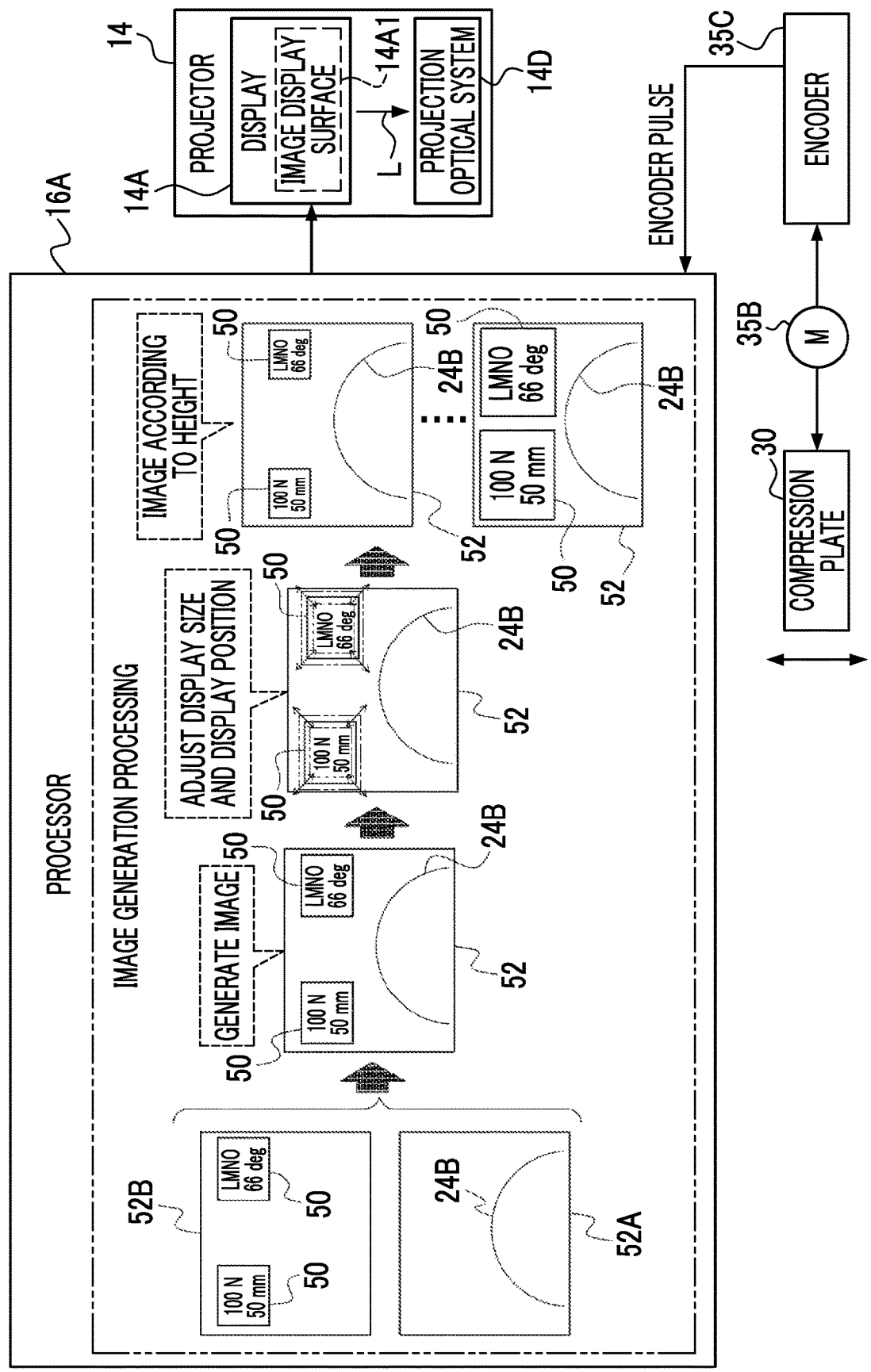
FIG. 8 is a functional block diagram showing an example of image generation processing in a processor.

As shown as an example in FIG. 8, the processor 16A executes image generation processing for generating the image 52 to be displayed on the display 14A. First, the processor 16A acquires the imaging condition information 50 in the image 52. For example, the processor 16A acquires the compression thickness t, the compression force, and the like of the imaging condition information 50 from a measurement value of the pressure measuring device and the height of the compression plate 30. In addition, the processor 16A acquires the imaging technique from input information of the operator. In addition, the processor 16A acquires information about the skin line 24B (coordinate information representing a shape and a position of the skin line 24B) derived from the examination image of the breast M imaged in the past. Then, based on the acquired imaging condition information 50 and skin line 24B, the processor 16A generates images 52A and 52B representing the imaging condition information 50 and the skin line 24B. Then, the processor 16A combines the two images 52A and 52B to generate the image 52 including the imaging condition information 50 and the skin line 24B.

Further, the processor 16A adjusts the display size and the display position of the imaging condition information 50 in the generated image 52 in accordance with the position of the compression plate 30 and the projection range R on the compression plate 30. On the other hand, since the projection distance to the imaging surface 24A is fixed, in the image 52, the adjustment of the display size and the display position according to the position of the compression plate 30 is not performed for the skin line 24B to be projected onto the imaging surface 24A. That is, the processor 16A adjusts the display size and the display position for the imaging condition information 50 independently of the adjustment for the display size and the display position of the skin line 24B in the image 52.

As described above, the processor 16A detects the movement amount of the compression plate 30 by counting the encoder pulse from the encoder 35C (see FIG. 3) of the drive mechanism 35. Then, the position of the compression plate 30 is obtained in accordance with the detected movement amount. The processor 16A adjusts the display size and the display position of the imaging condition information 50 in the image 52 based on the position of the compression plate 30. In this way, the image 52 according to the position of the compression plate 30 (that is, a height from the imaging surface 24A) is generated. In FIG. 8, the image 52 according to the height generated by the image generation processing shows how the display position and the display size of the imaging condition information 50 change in accordance with the position of the compression plate 30.

The processor 16A outputs a signal indicating the image 52 according to the position of the compression plate 30 to the display 14A of the projector 14. The display 14A displays the image 52 on the image display surface 14A1 based on the signal acquired from the processor 16A. Then, the projector 14 emits the projection light L indicating the image 52 via the built-in optical system 14B.

Projection conditions for each piece of information projected by the projector 14 described above, that is, the projection location, the focus, the display position, and the display size are summarized in FIG. 9. First, the projection location of the skin line 24B is the imaging surface 24A, and the display position and the display size of the skin line 24B in the image 52 are fixed. On the other hand, the projection location of the imaging condition information 50 is the bottom surface 30A of the compression plate 30, and the display position and the size are adjusted in accordance with the height of the compression plate 30. Specifically, the lower the position of the compression plate 30 (that is, the height from the imaging surface 24A), the longer the projection distance. Since a magnification ratio of the image 52 increases relatively as the projection distance increases, the display size of the image 52 displayed on the display 14A decreases in consideration of the increase of the magnification ratio. In addition, the higher the position of the compression plate 30, the shorter the projection distance. Since the magnification ratio of the image 52 decreases relatively as the projection distance decreases, the display size of the image 52 displayed on the display 14A increases in consideration of the decrease of the magnification ratio. The focus of the projection optical system 14D in the projector 14 is adjusted within a range between the imaging surface 24A and a position close to the projector 14 from the imaging surface 24A by the statistically determined thickness t of the breast M and thus is fixed. Further, the projection magnification of the projection optical system 14D is also fixed.

Figure 10:
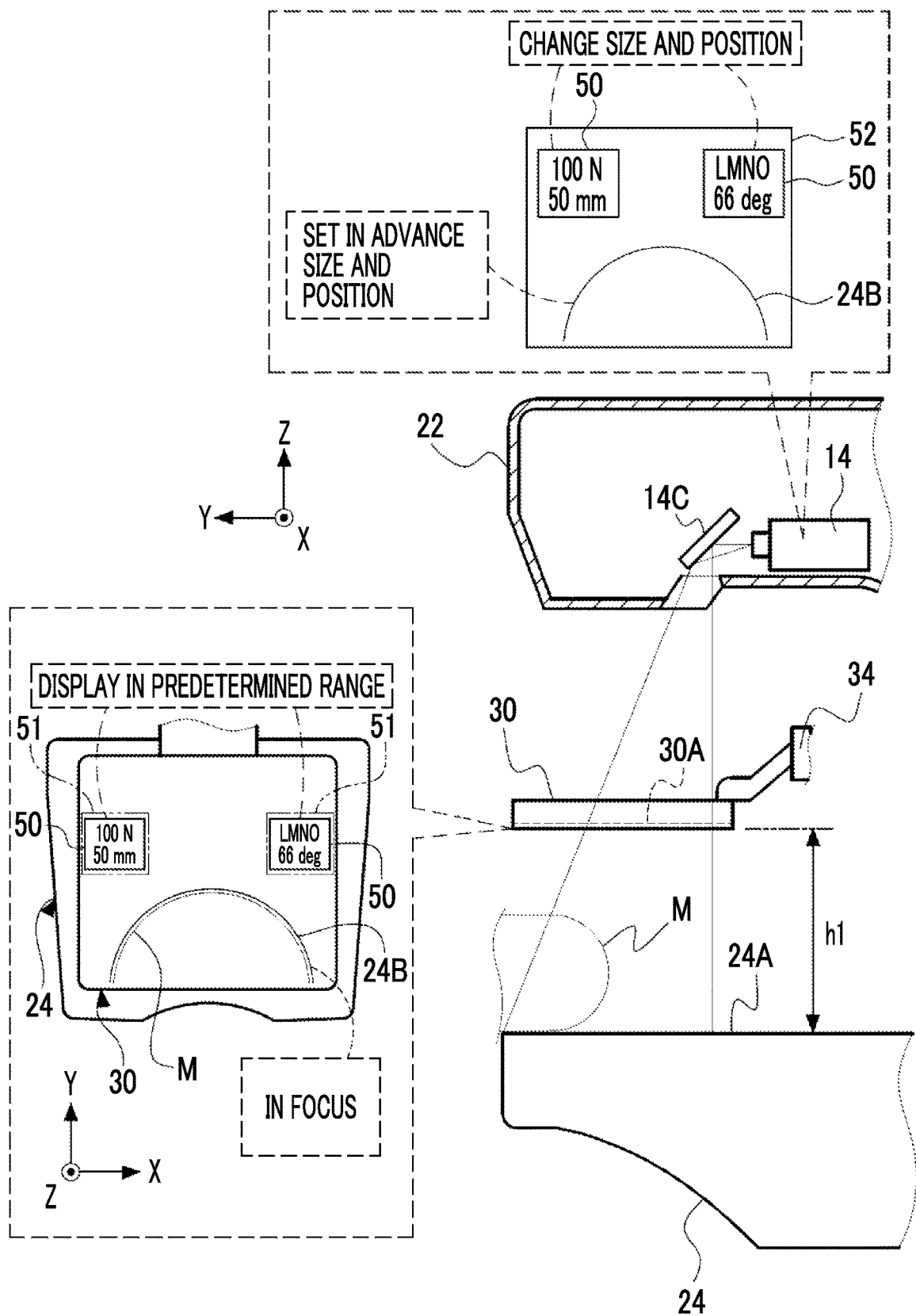
FIG. 10 is a side view showing an example of the projection of the image in the mammography apparatus.

Next, an operation of the mammography apparatus 10 according to the present embodiment will be described with reference to FIGS. 10 and 11. As shown in FIG. 10, first, a state in which the compression plate 30 is at a position closest to the projector 14 (that is, a distance h1 from the imaging surface 24A) is considered. In this case, the display size and the display position of the skin line 24B are set in advance in the image 52 on the image display surface 14A1 of the display 14A. For example, in a case where the skin line 24B indicates a position of the breast M, which is placed in the past imaging, on the imaging surface 24A, the display size of the skin line 24B of the image 52 is adjusted to be the same size as an actual size of the breast on the imaging surface 24A. In addition, the display position of the skin line 24B of the image 52 is adjusted to be the same as the position of the breast M, which is placed in the past imaging, on the imaging surface 24A. The display position and the display size of the skin line 24B adjusted in this manner are fixed even in a case where the position of the compression plate 30 changes. In other words, as will be described later, the display size and the display position of the skin line 24B are fixed even in a case where the display size or the display position of the imaging condition information 50 changes in accordance with the movement of the compression plate 30.

On the other hand, in the image 52 on the image display surface 14A1, the display size and the display position of the imaging condition information 50 are adjusted in accordance with the position of the compression plate 30 (that is, the distance h1 from the imaging surface 24A). Since the compression plate 30 is located at a position closest to the projector 14, the display size of the imaging condition information 50 is adjusted to be the largest in the image 52. In addition, in a case where it is necessary to adjust the display position by the compression plate 30, the display position of the imaging condition information 50 is also changed. For example, there may be a case where the projection position of the imaging condition information 50 on the compression plate 30 is to be projected at a position as far away from the breast M as possible, that is, on a counter-chest wall side (an opposite side of a chest wall of the subject). In this case, in a case where the display size of the imaging condition information 50 is relatively reduced, a gap is generated on the counter-chest wall side of the compression plate 30. Therefore, the display position of the imaging condition information 50 is moved toward the counter-chest wall side so as to fill the gap.

Then, the image 52 is projected from the projector 14 onto the compression plate 30 and the imaging surface 24A. The imaging condition information 50 whose display size and display position are adjusted in accordance with the position of the compression plate 30 is projected onto the compression plate 30. For example, the imaging condition information 50 is projected within the region 51 of the compression plate 30 that has been subjected to processing for suppressing the transmission of light. In addition, the skin line 24B is projected onto the imaging surface 24A. Since the focus of the built-in optical system 14B of the projector 14 is on the imaging surface 24A, the skin line 24B is projected onto the imaging surface 24A in a state in which the skin line 24B is in focus.

In this case, since the skin line 24B is in focus, the contour of the breast M can be aligned with the skin line 24B. In addition, since the imaging condition information 50 is projected onto the compression plate 30, the user can check the imaging conditions while performing registration of the breast M. In this case, the imaging condition information 50 projected onto the compression plate 30 is out of focus. However, since the compression plate 30 is located on a short-range side of the imaging surface 24A that is in focus, a degree of blurriness is small as compared with a long-range side of the in-focus position. Therefore, it is possible to perform appropriate projection with good visibility even for the imaging conditions.

Figure 11:
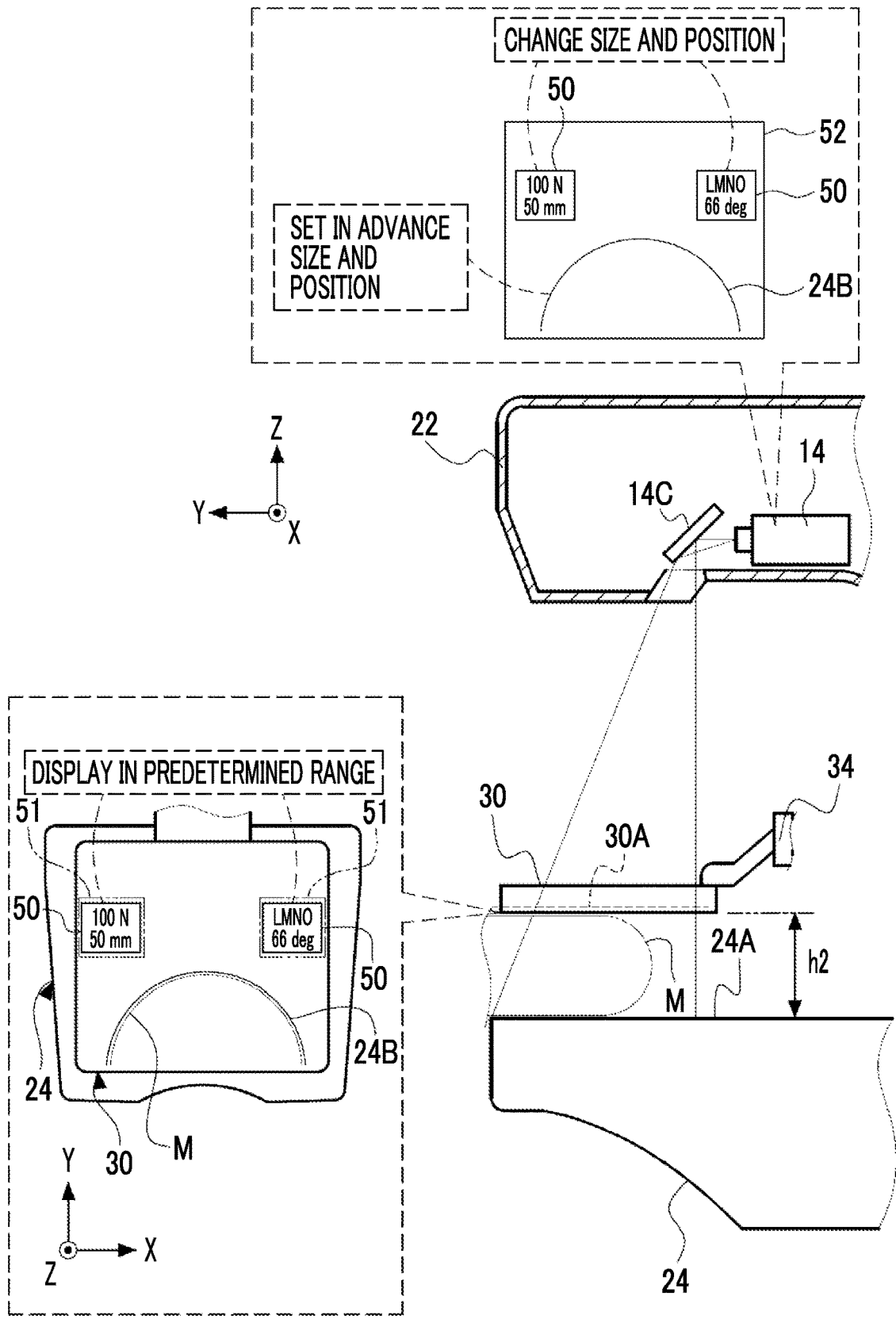
FIG. 11 is a side view showing an example of the projection of the image in the mammography apparatus.

Next, as shown in FIG. 11, a state in which the compression plate 30 is at a position moved in a direction away from the projector 14 (that is, a distance h2<h1 from the imaging surface 24A) is considered. In this case, the display size and the display position of the skin line 24B in the image 52 on the image display surface 14A1 of the display 14A remain fixed. That is, the skin line 24B is displayed in the image 52 with the same settings as in a state in which the compression plate 30 is located at a position closest to the projector 14.

In the image 52, the display size and the display position of the imaging condition information 50 are adjusted in accordance with the position of the compression plate 30 (that is, the distance h2 from the imaging surface 24A). Since the compression plate 30 has moved to a position distant from the projector 14 (that is, has moved to a position of the distance h2 from the distance h1 from the imaging surface 24A), the projection distance to the compression plate 30 becomes long. Then, the display size of the imaging condition information 50 is adjusted to be smaller in the image 52 in accordance with the increase in the projection distance to the compression plate 30. In addition, in a case where it is necessary to change the display position in accordance with the adjustment of the display size of the imaging condition information 50, the display position of the imaging condition information 50 is also changed. For example, the processor 16A adjusts the display size and the display position of the imaging condition information 50 in the image 52 on the image display surface 14A1 by controlling the display 14A in accordance with the position of the compression plate 30 and the projection range on the compression plate 30.

Then, the image 52 is projected from the projector 14 onto the compression plate 30 and the imaging surface 24A. The imaging condition information 50 whose display size and display position are adjusted in accordance with the position of the compression plate 30 is projected onto the compression plate 30. That is, the imaging condition information 50 is displayed on the compression plate 30 at the same display size and display position as the display size and display position before the compression plate 30 is moved. For example, the imaging condition information 50 is projected within the region 51 of the compression plate 30 that has been subjected to processing for suppressing the transmission of light. In addition, the skin line 24B is projected onto the imaging surface 24A. Since the focus of the built-in optical system 14B of the projector 14 is on the imaging surface 24A, the skin line 24B is projected onto the imaging surface 24A in a state in which the skin line 24B is in focus.

In this case, since the skin line 24B is in focus, the contour of the breast M can be aligned with the skin line 24B. In addition, since the imaging condition information 50 is projected onto the compression plate 30, the user can check the imaging conditions while performing registration of the breast M. In this case, the display size and the display position of the imaging condition information 50 projected onto the compression plate 30 are adjusted in accordance with the position of the compression plate 30. Therefore, during the compression of the breast M by the compression plate 30, the imaging condition information 50 can be continuously displayed in the same region. Therefore, it is possible to perform appropriate projection with good visibility even for the imaging conditions.

Here, a case where the position of the compression plate 30 is a position closest to the projector 14 (that is, the distance h1 from the imaging surface 24A) and a case where the position of the compression plate 30 is a position where the compression plate 30 compresses the breast M (that is, the distance h2 from the imaging surface 24A) has been described above. However, the display size and the display position of the imaging condition information 50 are adjusted even in a case where the compression plate 30 is located at a position other than those of the above cases. In a case where the compression plate 30 moves between the radiation source 25 and the imaging table 24, the display size and the display position of the imaging condition information 50 are adjusted in accordance with the movement of the compression plate 30.

As described above, with the mammography apparatus 10 according to the present embodiment, it is possible to project each of the skin line 24B projected onto the imaging table 24 and the imaging condition information 50 projected onto the compression plate 30 while maintaining the visibility of the imaging condition information 50 without complicating the projector 14 or the projection optical system, as compared with a case where both focus adjustment and adjustment of the position and size of projection are performed. That is, the focus of the built-in optical system 14B of the projector 14 is adjusted in accordance with the projection distance to the imaging surface 24A. Thus, it is possible to simplify the configuration of the projector 14. In addition, in a case where two pieces of information having different projection distances (that is, the imaging condition information 50 and the skin line 24B) are projected by one projector 14, comparing a degree of blurriness on one of a short-range side and a long-range side in a case where the other is in focus, the degree of blurriness on the short-range side in a case where the long-range side is in focus is smaller. Therefore, by adjusting the focus to the imaging table 24 on which the skin line 24B is projected as in the above configuration, it is possible to suppress a decrease in visibility of the imaging condition information 50.

In addition, in the mammography apparatus 10 according to the present embodiment, the display size and the display position of the skin line 24B projected onto the imaging surface 24A are set in advance in accordance with the projection distance to the imaging surface 24A. As a result, the configuration of the projector 14 can be simplified as compared with a case where the display size and the display position of the skin line 24B are adjusted in addition to the imaging condition information 50.

In addition, with the mammography apparatus 10 according to the present embodiment, the focus of the built-in optical system 14B is adjusted within a range between the imaging surface 24A and a position close to the projector 14 side from the imaging surface 24A by the statistically determined thickness t of the breast M. Since the focus is adjusted within the above-described range, both the skin line 24B and the imaging condition information 50 can be well-balanced and good visibility can be ensured as compared with a case where the focus is adjusted outside the above-described range.

In addition, in the mammography apparatus 10 according to the present embodiment, since the focus is on the imaging surface 24A, good visibility can be ensured for the skin line 24B as compared with a case where the focus is on a part other than the imaging surface 24A.

In addition, in the mammography apparatus 10 according to the present embodiment, a region on which the imaging condition information 50 is projected is subjected to light transmission suppression processing for suppressing transmission of the projection light L in the compression plate 30. Accordingly, the visibility of the imaging condition information 50 projected onto the compression plate 30 is improved as compared with a case where the light transmission suppression processing is not performed.

In addition, in the mammography apparatus 10 according to the present embodiment, the information projected onto the imaging surface 24A is the skin line 24B indicating the contour of the breast M, which is an index for placing the breast M. Since the skin line 24B is displayed on the imaging surface 24A, a positioning accuracy in a case where the breast M is placed on the imaging table 24 is improved as compared with a case where the skin line 24B is not displayed.

In addition, in the mammography apparatus 10 according to the present embodiment, the imaging condition information 50 is an imaging condition for imaging the breast M. Since the imaging condition is displayed on the compression plate 30, it is easy to check the imaging condition as compared with a case where the imaging condition is not displayed.

The above embodiment has been described with an example of a form in which both the display size and the display position of the imaging condition information 50 are adjusted in accordance with the movement of the compression plate 30, but the technology of the present disclosure is not limited thereto. An aspect in which one of the display size or the display position of the imaging condition information 50 is adjusted in accordance with the movement of the compression plate 30 may be employed.

In addition, the above embodiment has been described with an example of a form in which the display size and the display position of the skin line 24B are set in advance in the image 52 on the image display surface 14A1 of the display 14A, but the technology of the present disclosure is not limited thereto. For example, the display size and the display position of the skin line 24B may be set once and then adjusted based on an input from the user.

In addition, the above embodiment has been described with an example of a form in which, the imaging condition information 50 is projected onto the compression plate 30, and the skin line 24B is displayed on the imaging surface 24A, but the technology of the present disclosure is not limited thereto. For example, an aspect in which the imaging condition information 50 and the skin line 24B are displayed on the compression plate 30 may be employed. In this case, a region on which the skin line 24B is displayed is also subjected to the light transmission suppression processing in the compression plate 30. However, in this case, since the breast M is difficult to be seen through the compression plate 30, as described in the above-described embodiment, an aspect in which the projection light L is transmitted through the compression plate 30 and the skin line 24B is displayed on the imaging surface 24A is more preferable.

The various processors include a graphics processing unit (GPU) in addition to a CPU. In addition, the various processors are not limited to a general-purpose processor such as a CPU that functions as various processing units by executing software (program), and include a programmable logic device (PLD) which is a processor capable of changing a circuit configuration after manufacture such as a field programmable gate array (FPGA), a dedicated electric circuit which is a processor having a circuit configuration exclusively designed to execute specific processing such as an application specific integrated circuit (ASIC), and the like.

Furthermore, as the hardware structure of the various processors, more specifically, an electric circuitry in which circuit elements such as semiconductor elements are combined can be used.

The above-described contents and illustrated contents are detailed descriptions of parts related to the technology of the present disclosure, and are merely examples of the technology of the present disclosure. For example, the above descriptions related to configurations, functions, operations, and advantages effects are descriptions related to examples of configurations, functions, operations, and advantages effects of the parts related to the technology of the present disclosure. Therefore, it is needless to say that unnecessary parts may be deleted, or new elements may be added or replaced with respect to the above-described contents and illustrated contents within a scope not departing from the spirit of the technology of the present disclosure. In order to avoid complication and easily understand the parts according to the technology of the present disclosure, in the above-described contents and illustrated contents, common technical knowledge and the like that do not need to be described to implement the technology of the present disclosure are not described.

All documents, patent applications, and technical standards described in the present specification are incorporated in the present specification by reference to the same extent as in a case where each document, patent application, and technical standard are specifically and individually noted to be incorporated by reference.

Furthermore, the following appendices will be disclosed in relation to the above-described embodiment.

APPENDIX 1

A mammography apparatus comprising: an imaging table on which a breast is placed; a radiation source that emits radiation toward the breast; a compression plate that compresses the breast on the imaging table and is movable between the radiation source and the imaging table; a projector that includes a display displaying an image including first information projected onto a first surface facing the radiation source on the imaging table and second information projected onto a second surface facing the radiation source on the compression plate, and a projection optical system projecting the image toward the first surface and the second surface, in which a focus of the projection optical system is adjusted in accordance with a projection distance to the first surface; and a processor that is configured to control the display and change at least one of a display size or a display position of the second information in the image on an image display surface of the display in accordance with movement of the compression plate having the second surface independently of the first information.

APPENDIX 2

The mammography apparatus according to appendix 1, in which a display size and a display position of the first information in the image are set in advance in accordance with the projection distance to the first surface and are fixed even in a case where the display size or the display position of the second information changes.

APPENDIX 3

The mammography apparatus according to appendix 1 or 2, in which the focus of the projection optical system is adjusted within a range between the first surface and a position close to a projector side from the first surface by a statistically determined thickness of the breast.

APPENDIX 4

The mammography apparatus according to any one of appendices 1 to 3, in which the focus of the projection optical system is adjusted to the first surface.

APPENDIX 5

The mammography apparatus according to any one of appendices 1 to 4, in which, on the second surface of the compression plate, a region onto which the second information is projected is subjected to light transmission suppression processing for suppressing transmission of light.

APPENDIX 6

The mammography apparatus according to any one of appendices 1 to 5, in which the first information is a skin line indicating a contour of the breast, which is an index for placing the breast.

APPENDIX 7

The mammography apparatus according to any one of appendices 1 to 6, in which the second information is an imaging condition for imaging the breast.

What is claimed is:
1. A mammography apparatus comprising:
an imaging table on which a breast is placed;
a radiation source that emits radiation toward the breast;
a compression plate that compresses the breast on the imaging table and is movable between the radiation source and the imaging table;
a projector that includes a display displaying an image including first information projected onto a first surface facing the radiation source on the imaging table and second information projected onto a second surface facing the radiation source on the compression plate, and a projection optical system projecting the image toward the first surface and the second surface, in which a focus of the projection optical system is adjusted in accordance with a projection distance to the first surface; and
a processor that is configured to control the display and change at least one of a display size or a display position of the second information in the image on an image display surface of the display in accordance with movement of the compression plate having the second surface independently of the first information.
2. The mammography apparatus according to claim 1, wherein a display size and a display position of the first information in the image are set in advance in accordance with the projection distance to the first surface and are fixed even in a case where the display size or the display position of the second information changes.

3. The mammography apparatus according to claim 1, wherein the focus of the projection optical system is adjusted within a range between the first surface and a position close to a projector side from the first surface by a statistically determined thickness of the breast.

4. The mammography apparatus according to claim 3, wherein the focus of the projection optical system is adjusted to the first surface.

5. The mammography apparatus according to claim 1, wherein, on the second surface of the compression plate, a region onto which the second information is projected is subjected to light transmission suppression processing for suppressing transmission of light.

6. The mammography apparatus according to claim 1, wherein the first information is a skin line indicating a contour of the breast, which is an index for placing the breast.

7. The mammography apparatus according to claim 1, wherein the second information is an imaging condition for imaging the breast.

* * * * *